United States Patent [19]

Iwata et al.

[11] Patent Number: 4,665,172

[45] Date of Patent: * May 12, 1987

[54] PROCESS FOR PRODUCING HETEROCYCLIC COMPOUND HAVING NITROMETHYLENE GROUP AS THE SIDE CHAIN GROUP

[75] Inventors: Fumio Iwata; Katsumasa Harada; Ryoji Sugise, all of Ube, Japan

[73] Assignee: UBE Industries, Ltd., Ube, Japan

[*] Notice: The portion of the term of this patent subsequent to Nov. 25, 2003 has been disclaimed.

[21] Appl. No.: 569,983

[22] Filed: Jan. 11, 1984

[30] Foreign Application Priority Data

Jan. 28, 1983 [JP] Japan ............................ 58-11356
Nov. 29, 1983 [JP] Japan ............................ 58-223340

[51] Int. Cl.$^4$ ............... C07D 277/04; C07D 279/06; C07D 281/02
[52] U.S. Cl. .................................... 540/544; 544/53; 548/146
[58] Field of Search .............. 544/53; 548/146; 260/330; 540/544

[56] References Cited

U.S. PATENT DOCUMENTS

| | | | |
|---|---|---|---|
| 3,247,224 | 4/1966 | Enders et al. | 260/330 |
| 3,933,809 | 1/1976 | Powell | 544/53 |
| 3,962,225 | 6/1976 | Powell | 544/53 |
| 3,993,648 | 11/1976 | Powell | 544/53 |
| 4,006,156 | 2/1977 | Powell | 548/146 |
| 4,264,614 | 4/1981 | Cletheron et al. | 549/495 |
| 4,279,819 | 6/1981 | Price et al. | 549/495 |

OTHER PUBLICATIONS

Rajappa, S. et al: Nitroenamines, Part 9, The Enamic Reactivity of 2-Nitromethylenethiazolidine, CA 99: 70613v, Proc.-Indian Acad. Sci., (1982).
March, Advanced Organic Chem.: Reactions, Mechanisms and Structure, 2nd Edition, 1977, McGraw, Hill, NY, p. 916.

Primary Examiner—Glennon H. Hollrah
Assistant Examiner—D. L. Dinner
Attorney, Agent, or Firm—Frishauf, Holtz, Goodman & Woodward

[57] ABSTRACT

Disclosed is a process for producing a heterocyclic compound having as the side chain group a nitromethylene group of the formula:

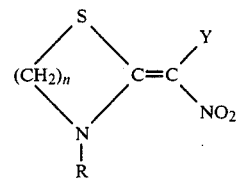

wherein Y, R and n are as defined in the specification, which comprises reacting a 2,2-dihalonitroethylene compound with a 1-aminoalkanethiol compound or a 1-N-substituted derivative thereof.

13 Claims, No Drawings

PROCESS FOR PRODUCING HETEROCYCLIC COMPOUND HAVING NITROMETHYLENE GROUP AS THE SIDE CHAIN GROUP

BACKGROUND OF THE INVENTION

This invention relates to a novel process for producing a heterocyclic compound having a nitromethylene group as the side chain group.

Heterocyclic compounds having a nitromethylene group as the side chain group find uses in agricultural chemicals, pharmaceuticals or perfumes. For example, Japanese Unexamined Patent Publicaion No. 151882/1975 proposes tetrahydro-2-(nitromethylene)-1,3-thiazines having excellent activities as agricultural chemicals such as pesticides and acaricides.

In the prior art, most of the processes for preparation of heterocyclic compounds having a nitromethylene group as the side chain employ as the starting material cyclic dithiocarbamic acid esters which can easily be synthesized and are also highly reactive.

For example, the above Unexamined Patent Publilcation discloses the following process as the process for preparation of tetrahydro-2-(nitromethylene)-1,3-thiazines.

First, tetrahydro-1,3-thiazine-2-thion is methylated with a methyl halide, the resultant tetrahydro-2-(methylthio)-1,3-thiazine is allowed to react with an alkyl nitroacetate in the presence of zinc ions to give an alkyl nitro(tetrahydro-1,3-thiazine-2-ylidene)acetate, which is then hydrolyzed in the presence of a base, followed by decarboxylation to prepare a desired product of tetrahydro-2-(nitromethylene)-1,3-thiazine.

As can be seen from this example, the process for preparation of a heterocyclic compound having a nitromethylene group as the side chain group, using a cyclic dithiocarbamic acid ester as the starting material involves reaction steps which are very lengthy and complicated, and methyl mercaptan which may cause offensive odor is generated in the step of reacting the methylated starting material with an alkyl nitroacetate. Thus, this process cannot necessarily be stated to be satisfactory in industrial application.

SUMMARY OF THE INVENTION

The present inventors have made extensive studies in order to establish a process for producing industrially advantageously a heterocyclic compound having a nitromethylene group as the side chain. As a result, it has now been found that a 2,2-dihalonitroethylene compound of the formula (I):

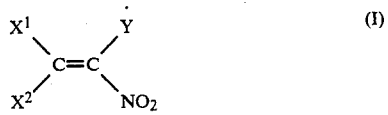

wherein $X^1$ and $X^2$ may be the same or different and represent halogen atoms, and Y represents a hydrogen atom, a halogen atom or a lower alkyl group, can be allowed to react with a 1-aminoalkanethiol compound or a 1-N-substituted derivative thereof of the formula (II):

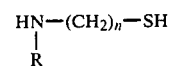

wherein R is a hydrogen atom, an alkyl group, a cycloalkyl group, an aralkyl group, an alkenyl group or an alkynyl group, and n represents an integer of 2, 3 or 4, in the presence of a base and in a solvent to produce industrially advantageously a heterocyclic compound having a nitromethylene group as the side chain group, of the formula (III):

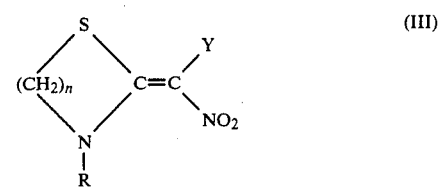

wherein Y represents a hydrogen atom, a halogen atom or a lower alkyl group, R represents a hydrogen atom, an alkyl group, a cycloalkyl group, an aralkyl group, an alkenyl group or an alkynyl group, and n represents an integer of 2, 3 or 4, to accomplish the present invention.

This invention is extremely simplified in the reaction step, as compared with the process of the prior art as described above, without by-production of methyl mercaptan, which will cause troubles in industrial practice of the process, and the desired product can be also obtained at a high yield.

DESCRIPTION OF THE PREFERRED EMBODIMENTS

In the 2,2-dihalonitroethylene compound represented by the above formula (I), which is the starting material to be used in this invention, the halogen atoms represented by $X^1$, $X^2$ and Y may be either the same or different, and they may be any of chlorine, bromine, fluorine and iodine. The lower alkyl group represented by Y may include alkyl groups having 1 to 4 carbon atoms such as methyl, ethyl, propyl and butyl.

Examples of the compound (I) are 2,2-dihalonitroethylenes such as 2,2-dichloronitroethylene, 2,2-dibromonitroethylene, 2,2-difluoronitroethylene, 2,2-diiodonitroethylene, 1-methyl-2,2-dichloronitroethylene, 1-ethyl-2,2-dichloronitroethylene, 2-bromo-2-chloronitroethylene, 1-methyl-2-bromo-2-chloronitroethylene, 1-ethyl-2-bromo-2-chloroethylene and 2-chloro-2-fluoronitroethylene; and 1,2,2-trihalonitroethylenes such as 1,2,2-trichloronitroethylene, 1,2,2-tribromonitroethylene, 1-bromo-2,2-dichloronitroethylene, 1-chloro-2-bromo-2-chloronitroethylene and 1,2-dichloro-2-bromonitroethylene.

Among them, in view of industrial availability, 2,2-dichloronitroethylene, 1,2,2-trichloronitroethylene and 1-alkyl-2,2-dichloronitroethylene are particularly useful.

These 2,2-dihalonitroethylene compounds can be readily synthesized according to the process known in the art. For example, in the case of the above-mentioned 2,2-dihalonitroethylene, it can be synthesized according to the reaction between a 2,2-dihaloethylene and a nitronium halide, while in the case of the above-mentioned 1,2,2-trihalonitroethylene, according to the reaction between a 1,2,2-trihaloethylene and nitric acid.

The 1-aminoalkanethiol or its 1-N-substituted derivative thereof represented by the above formula (II), which is the other starting material to be used in this invention, is a commercially available compound. Examples of the compound (II), when R is a hydrogen atom, are 1-amino-2-ethanethiol, 1-amino-3-propanethiol and 1-amino-4-butanethiol. The alkyl group represented by R may include alkyl groups having 1 to 12 carbon atoms such as methyl, ethyl, propyl, butyl, pentyl, hexyl, heptyl, octyl, nonyl, decyl, undecyl and dodecyl. As the cycloalkyl group, there may be included cycloalkyl groups having 5 to 12 carbon atoms such as cyclopentyl, cyclohexyl, cycloheptyl, cyclooctyl, cyclononyl, cyclodecyl, cycloundecyl and cyclododecyl. As the aralkyl group, there may be employed benzyl group and phenethyl group. Alkenyl groups may be, for example, those having 3 to 5 carbon atoms such as allyl, butenyl and pentenyl. Further, the alkynyl group may include those having 3 to 5 carbon atoms such as propargyl, butylyl and pentynyl.

Typical examples of the 1-N-substituted derivatives of 1-aminoalkanethiol are 1-methylamino-2-ethanethiol, 1-methylamino-3-propanethiol, 1-methylamino-4-butanethiol, 1-ethylamino-2-ethanethiol, 1-ethylamino-3-propanethiol, 1-ethylamino-4-butanethiol, 1-propylamino-2-ethanethiol, 1-propylamino-3-propanethiol, 1-propylamino-4-butanethiol, 1-isopropylamino-3-propanethiol, 1-butylamino-3-propanethiol, 1-pentylamino-3-propanethiol, 1-hexylamino-3-propanethiol, 1-octyl-amino-3-propanethiol, 1-decylamino-3-propanethiol, 1-dodecylamino-3-propanethiol, 1-cyclohexylamino-2-ethanethiol, 1-cyclohexylamino-3-propanethiol, 1-cyclohexylamino-4-butanethiol, 1-cylooctylamino-3-propanethiol, 1-cyclododecylamino-3-propanethiol, 1-benzylamino-2-ethanethiol, 1-benzylamino-3-propanethiol, 1-benzylamino-4-butanethiol, 1-allylamino-2-ethanethiol, 1-allylamino-3-propanethiol, 1-allylamino-4-butanethiol, 1-propargylamino-2-ethanethiol, 1-propargylamino-3-propanethiol.

These 1-aminoalkanethiol compounds or 1-N-substituted derivatives thereof may be used in an amount generally in the range of from 0.5 to 10 moles, preferably from 1 to 5 moles, per mole of the 2,2-dihalonitroethylene compound.

Useful bases to be used in this invention are alcoholates of alkali metals such as sodium methoxide, sodium ethoxide, potassium methoxide or potassium ethoxide; hydroxides of alkali metals such as sodium hydroxide or potassium hydroxide; hydroxides of alkaline earth metals such as calcium hydroxide, barium hydroxide or magnesium hydroxide. These bases can be used in amounts generally of 2 moles or more, preferably 2 to 5 moles, per mole of the 2,2-dihalonitroethylene provided for use.

The reaction in this invention is carried out in a solvent. As the solvent to be provided for use, any solvent may be useful, so long as it can dissolve both starting materials and the base at the same time and is inert to the reaction. Typical examples of the solvent may include lower aliphatic alcohols such as methanol, ethanol, i-propanol, n-propanol, i-butanol or n-butanol, water, dimethyl sulfoxide, acetonitrile and dimethylformamide. Among them, it is particularly preferred for industrial practice to employ a lower aliphatic alcohol as the solvent.

In the present invention, it is not necessary to provide restrictions with respect to the method by which a 2,2-dihalonitroethylene compound is brought into contact with 1-aminoalkanethiol compound or its 1-N-substituted derivative.

For example, a base may be added into a solution in which both starting materials are dissolved in a solvent. Alternatively, a 1-aminoalkanethiol compound or its 1-N-substituted derivative may be previously reacted with a base in a solvent to convert the thiol compound to a thiolate compound, followed by addition of a 2,2-dihalonitroethylene compound into the solution thereof. However, a desired compound can be obtained at still higher efficiency by employment of the method in which a 2,2-dihalonitroethylene and a base dissolved in separate solvents are added gradually, sometimes in divided portions, into a solution of a 1-aminoalkanethiol compound or its 1-N-substituted derivative.

The reaction according to this invention may be carried out at a temperature generally of 100° C. or lower, preferably of −10° to 50° C., for 0.5 to 10 hours, preferably 1 to 5 hours.

Thus, a heterocyclic compound having a nitromethylene group as the side chain can be obtained at a high yield. For example, when 1-amino-2-ethanethiol or 1-methylamino-2-ethanethiol is used as the 1-aminoalkanethiol compound or its 1-N-substituted derivative, there can be produced thiazolidines such as 2-(nitromethylene)-1,3-thiazolidine, 2-(nitro, chloromethylene)-1,3-thiazolidine, 3-methyl-2-(nitromethylene)-1,3-thiazolidine, 3-methyl-2-(nitro, chloromethylene)-1,3-thiazolidine and the like; and when 1-amino-3-propanethiol or 1-ethylamino-3-propanethiol is used, thiazines such as tetrahydro-2-(nitromethylene)-1,3-thiazine, tetrahydro-2-(nitro, chloromethylene)-1,3-thiazine, tetrahydro-3-ethyl-2-(nitromethylene)-1,3-thiazine, tetrahydro-3-ethyl- 2-(nitro, chloromethylene)-1,3-thiazine and the like; and further when 1-amino-4-butanethiol or 1-cyclohexylamino-4-butanethiol is used, thiazepines such as hexahydro-2-(nitromethylene)-1,3-thiazepine, hexahydro-2-(nitro, chloromethylene)-1,3-thiazepine, hexahydro-3-cyclohexyl-2-(nitromethylene)-1,3-thiazepine, hexahydro-3-cyclohexyl-2-(nitro, chloromethylene)-1,3-thiazepine and the like; respectively.

After completion of the reaction, isolation and purification of the desired product can be done easily by employing suitably such an operation as filtration, concentration, extraction or recrystallization. To describe more specifically by way of example, first after completion of the reaction, the reaction mixture is neutralized with an aqueous mineral acid solution and, after dilution of the neutralized solution with water, extracted with an organic solvent such as chloroform or dichloromethane. After removal of the solvent from the extract, the crude crystals obtained are recrystallized, whereby a purified desired product can be isolated.

Referring now to Examples, this invention is described in more detail. In each Example, the yield is based on the 2,2-dihalonitroethylene compound provided for use.

EXAMPLE 1

Into 40 ml of methanol were added 5.5 g of 1-amino-3-propanethiol and 2.4 g of caustic soda, followed by stirring, to be completely dissolved therein. Then, the mixture was cooled to 0° C. While stirring the solution, a solution of 2.8 g of 2,2-dichloronitroethylene diluted in 10 ml of methanol was added dropwise slowly over 15 minutes, and the reaction was carried out for one hour. The reaction was exothermic and the liquid temperature was maintained at lower than 10° C. (about 8° C.) After the reaction, the reaction mixture was neutralized to pH 7 with 6 N aqueous hydrochloric acid, and then with addition of 30 ml of water, extraction with 50 ml of chloroform was repeated four times. The extracts were concentrated to give 2.24 g of tetrahydro-2-(nitromethylene)-1,3-thiazine (yield: 70.0%).

EXAMPLE 2

An experiment was conducted according to the same procedure as in Example 1 except for using 13.5 g of a 28 wt. % methanolic solution of sodium methoxide in place of 2.4 g of caustic soda. As the result, 2.31 g of tetrahydro-2-(nitromethylene)-1,3-thiazine was obtained (yield: 72.2%).

EXAMPLE 3

An experiment was conducted according to the same procedure as in Example 1 except for using a 28 wt. % methanolic solution of sodium methoxide in place of 2.4 g of caustic soda and changing the amount of 1-amino-3-propanethiol employed to 3.5 g. As the result, 2.03 g of tetrahydro-2-(nitromethylene)-1,3-thiazine (yield: 63.5%) was obtained.

EXAMPLE 4

An experiment was conducted according to the same procedure as in Example 1 except for using 14.0 g of a 30 wt. % methanolic solution of potassium ethoxide in place of 2.4 g of caustic soda. As the result, 2.41 g of tetrahydro-2-(nitromethylene)-1,3-thiazine was obtained (yield: 75.2%).

EXAMPLE 5

Into 40 ml of methanol was added 5.5 g of 1-amino-3-propanethiol, followed by stirring, to be completely dissolved therein. Then, the mixture was cooled to 0° C. While stirring the solution, about ⅓-aliquot of a solution of 2.4 g of caustic soda dissolved in 20 ml of methanol was added dropwise thereinto, and the remainder of about 2/3-aliquot of the solution and a solution of 2.8 g of 2,2-dichloronitroethylene diluted in 10 ml of methanol were added dropwise slowly over 50 minutes, and the reaction was carried out for one hour. During the dropwise addition, the liquid temperature was maintained at lower than 10° C. (about 8° C.). After the reaction carried out for one hour, the procedure of the post-treatments as described in Example 1 was followed to obtain 2.96 g of tetrahydro-2-(nitromethylene)-1,3-thiazine (yield: 92.6%).

EXAMPLE 6

An experiment was conducted according to the same procedure as in Example 5 except for using 11.6 g of a 28 wt. % methanolic solution of sodium methoxide in place of a solution of 2.4 g of caustic soda dissolved in 20 ml of methanol. As the result, 2.94 g of tetrahydro-2-(nitromethylene)-1,3-thiazine was obtained (yield: 92.0%).

EXAMPLE 7

An experiment was conducted according to the same procedure as in Example 5 except for using 11.6 g of a 28 wt. % methanolic solution of sodium methoxide in place of a solution of 2.4 g of caustic soda dissolved in 20 ml of methanol and changing the amount of 1-amino-3-propanethiol employed to 3.5 g. As the result, 2.61 g of tetrahydro-2-(nitromethylene)-1,3-thiazine (yield: 81.6%) was obtained.

EXAMPLE 8

An experiment was conducted according to the same procedure as in Example 5 except for using a solution of 3.4 g of potassium hydroxide dissolved in 20 ml of methanol in place of a solution of 2.4 g of caustic soda dissolved in 20 ml of methanol. As the result, 2.86 g of tetrahydro-2-(nitromethylene)-1,3-thiazine was obtained (yield: 89.3%).

EXAMPLE 9

An experiment was conducted according to the same procedure as in Example 5 except for using 4.6 g of 2,2-dibromonitroethylene in place of 2.8 g of 2,2-dichloronitroethylene. As the result, 2.80 g of tetrahydro-2-(nitromethylene)-1,3-thiazine was obtained (yield: 87.5%).

EXAMPLE 10

An experiment was conducted according to the same procedure as in Example 5 except for using 3.6 g of 1,2,2-trichloronitroethylene in place of 2.8 g of 2,2-dichloronitroethylene. As the result, 3.3 g of tetrahydro-2-(nitro, chloromethylene)-2,3-thiazine was obtained (yield: 85.0%).

EXAMPLE 11

An experiment was conducted according to the same procedure as in Example 4 except for using 4.6 g of 1-amino-2-ethanethiol in place of 1-amino-3-propanethiol. As the result, 2.26 g of 2-(nitromethylene)-1,3-thiazolidine was obtained (yield: 77.3%).

EXAMPLE 12

An experiment was conducted according to the same procedure as in Example 5 except for using 6.3 g of 1-amino-4-butanethiol in place of 1-amino-3-propanethiol. As the result, 3.14 g of 2-(hexahydronitromethylene)-1,3-thiazepine was obtained (yield: 90.3%).

EXAMPLE 13

Into 40 ml of methanol were added 5.0 g of 1-methylamino-3-propanethiol and 0.8 g of caustic soda, followed by stirring, to be completely dissolved therein. Then, the mixture was cooled to 0° C. While stirring the solution, a solution of 1.6 g of caustic soda dissolved in 25 ml of methanol and a solution of 2.8 g of 2,2-dichloronitroethylene diluted in 20 ml of methanol were added at the same time dropwise slowly over 50 minutes, and the reaction was carried out for one hour at about 8° C. After the reaction, the reaction mixture was neutralized to pH 7 with 3 N aqueous hydrochloric acid, and then with addition of 60 ml of water, extraction with 50 ml of methylene chloride was repeated four times. The extracts were concentrated to give 3.38 g of tetrahydro-3-methyl-2-(nitromethylene)-1,3-thiazine (yield: 97%).

EXAMPLE 14

An experiment was conducted according to the same procedure as in Example 13 except for using 11.6 g of 28 wt. % methanolic solution of sodium methoxide in place of caustic soda. As the result, 3.41 g of tetrahydro- 3-methyl- 2-(nitromethylene)-1,3-thiazine (yield: 98%) was obtained.

EXAMPLE 15

An experiment was conducted according to the same procedure as in Example 13 except for using 5.6 g of 1-ethylamino-3-propanethiol in place of 1-methylamino-3-propanethiol. As the result, 3.65 g of tetrahydro-3-ethyl-2-(nitromethylene)-1,3-thiazine was obtained (yield: 97%).

EXAMPLE 16

An experiment was conducted according to the same procedure as in Example 15 except for using 3.4 g of caustis potash in place of caustic soda. As the result, 3.66 g of tetrahydro-3-ethyl-2-(nitromethylene)-1,3-thiazine (yield: 97%) was obtained.

EXAMPLE 17

An experiment was conducted according to the same procedure as in Example 13 except for using 6.3 g of 1-isopropylamino-3-propanethiol in place of 1-methylamino-3-propanethiol. As the result, 3.92 g of tetrahydro-3-isopropyl-2-(nitromethylene)-1,3-thiazine was obtained (yield: 97%).

EXAMPLE 18

An experiment was conducted according to the same procedure as in Example 13 except for using 8.3 g of 1-n-hexylamino-3-propanethiol in place of 1-methylamino-3-propanethiol. As the result, 4.68 g of tetrahydro-3-n-hexyl- 2-(nitromethylene)-1,3-thiazine was obtained (yield: 96%).

EXAMPLE 19

An experiment was conducted according to the same procedure as in Example 13 except for using 8.2 g of 1-cyclohexylamino-3-propanethiol in place of 1-methylamino-3-propanethiol. As the result, 4.69 g of tetrahydro-3-cyclohexyl-2-(nitromethylene)-1,3-thiazine was obtained (yield: 97%).

EXAMPLE 20

Example 19 was repeated except that 14.0 g of a 30 wt. % methanolic solution of potassium methoxide was employed in place of caustic potash. As the result, 4.70 g of tetrahydro-3-cyclohexyl-2-(nitromethylene)-1,3-thiazine was obtained (yield: 97%).

EXAMPLE 21

An experiment was conducted according to the same procedure as in Example 13 except for using 8.6 g of 1-benzylamino-3-propanethiol in place of 1-methylamino-3-propanethiol. As the result, 4.75 g of tetrahydro-3-benzyl-2-(nitromethylene)-1,3-thiazine was obtained (yield: 95%).

EXAMPLE 22

An experiment was conducted according to the same procedure as in Example 13 except for using 6.2 g of 1-allylamino-3-propanethiol in place of 1-methylamino-3-propanethiol. As the result, 3.84 g of tetrahydro-3-allyl- 2-(nitromethylene)-1,3-thiazine was obtained (yield: 96%).

EXAMPLE 23

An experiment was conducted according to the same procedure as in Example 13 except for using 6.1 g of 1-propargylamino-3-propanethiol in place of 1-methylamino-3-propanethiol. As the result, 3.76 g of tetrahydro-3-propargyl-2-(nitromethylene)-1,3-thiazine was obtained (yield: 95%).

EXAMPLE 24

An experiment was conducted according to the same procedure as in Example 13 except for using 4.6 g of 2,2-dibromonitroethylene in place of 2,2-dichloronitroethylene. As the result, 3.36 g of tetrahydro-3-methyl-2-(nitromethylene)-1,3-thiazine was obtained (yield: 96%).

EXAMPLE 25

An experiment was conducted according to the same procedure as in Example 13 except for using 3.5 g of 1,2,2-trichloronitroethylene in place of 2,2-dichloronitroethylene. As the result, 3.97 g of tetrahydro-3-methyl-2-(nitro, chloromethylene)-1,3-thiazine was obtained (yield: 95%).

EXAMPLE 26

An experiment was conducted according to the same procedure as in Example 25 except for using 5.6 g of 1-ethylamino-3-propanethiol in place of 1-methylamino-3-propanethiol. As the result, 4.18 g of tetrahydro-3-ethyl- 2-(nitro, chloromethylene)-1,3-thiazine was obtained (yield: 94%).

EXAMPLE 27

An experiment was conducted according to the same procedure as in Example 25 except for using 8.2 g of 1-cyclohexylamino-3-propanethiol in place of 1-methylamino-3-propanethiol. As the result, 5.31 g of tetrahydro-3-cyclohexyl-2-(nitro, chloromethylene)-1,3-thiazine was obtained (yield: 96%).

EXAMPLE 28

An experiment was conducted according to the same procedure as in Example 25 except for using 8.6 g of 1-benzylamino-3-propanethiol in place of 1-methylamino-3-propanethiol. As the result, 5.41 g of tetrahydro-3-benzyl-2-(nitro, chloromethylene)-1,3-thiazine was obtained (yield: 95%).

EXAMPLE 29

An experiment was conducted according to the same procedure as in Example 25 except for using 6.2 g of 1-allylamino-3-propanethiol in place of 1-methylamino-3-propanethiol. As the result, 4.46 g of tetrahydro-3-allyl-2-(nitro, chloromethylene)-1,3-thiazine was obtained (yield: 95%).

EXAMPLE 30

An experiment was conducted according to the same procedure as in Example 25 except for using 6.1 g of 1-propargylamino-3-propanethiol in place of 1-methylamino-3-propanethiol. As the result, 4.37 g of tetrahydro-3-propargyl-2-(nitro, chloromethylene)-1,3-thiazine was obtained (yield: 94%).

EXAMPLE 31

An experiment was conducted according to the same procedure as in Example 13 except for using 4.3 g of 1-methylamino-2-ethanethiol in place of 1-methylamino-3-propanethiol. As the result, 2.88 g of 3-methyl-2-(nitromethylene)-1,3-thiazolidine was obtained (yield: 90%).

EXAMPLE 32

An experiment was conducted according to the same procedure as in Example 13 except for using 5.6 g of 1-methylamino-2-butanethiol in place of 1-methylamino-3-propanethiol. As the result, 3.38 g of hexahydro-3-methyl-2-(nitromethylene)-1,3-thiazepine was obtained (yield: 90%).

We claim:

1. A process for producing a heterocyclic compound having a nitromethylene group as the side chain, of the formula (III):

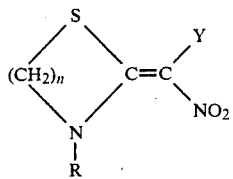

wherein Y represents a hydrogen atom, a halogen atom or a $C_1$–$C_4$ alkyl group, R represents a hydrogen atom, a $C_1$–$C_{12}$ alkyl group, a cycloalkyl group having 5 to 12 carbon atoms, a benzyl group, a phenethyl group, a $C_3$–$C_5$ alkenyl group or a $C_3$–$C_5$ alkynyl group, and n represents an integer of 2, 3 or 4,
which comprises reacting a 2,2-dihalonitroethylene compound of the formula (I):

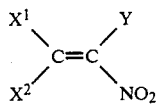

wherein $X^1$ and $X^2$ may be the same or different and represent halogen atoms,
with a 1-aminoalkanethiol compound or a 1-N-substituted derivative thereof, of the formula (II):

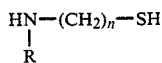

in the presence of a base and in a solvent which dissolves both reactants and the base.

2. The process according to claim 1, whrein said compound of the formula (II) is used in an amount of from 0.5 to 10 moles per mole of the compound of the formula (I).

3. The process according to claim 1, wherein said base is selected from the group consisting of sodium methoxide, sodium ethoxide, potassium methoxide, potassium ethoxide, sodium hydroxide, potassium hydroxide, calcium hydroxide, barium hydroxide, and magnesium hydroxide.

4. The process according to claim 3, wherein said base is used in an amount of 2 to 5 moles per mole of the compound of the formula (I).

5. The process according to claim 1, wherein said solvent is selected from the group consisting of methanol, ethanol, i-propanol, n-propanol, i-butanol, n-butanol, water, dimethyl sulfoxide, acetonitrile and dimethylformamide.

6. The process according to claim 1, wherein the reaction is carried out at a temperature of from $-10°$ to $50°$ C. for 0.5 to 10 hours.

7. The process according to claim 1, wherein the compound of the formula (I) is selected from the group consisting of 2,2-dichloronitroethylene, 2,2-dibromonitroethylene, and 1,2,2-trichloronitroethylene.

8. The process according to claim 1, wherein the compound of the formula (II) is selected from the group consisting of 1-amino-2-ethanethiol, 1-amino-3-propanethiol, 1-amino-4-butanethiol, 1-methylamino-3-propanethiol, 1-methylamino-4-butanethiol, 1-ethylamino-2-ethanethiol, 1-ethylamino-3-propanethiol, 1-isopropyl-amino-3-propanethiol, 1-hexylamino-3-propanethiol, 1-cyclohexylamino-3-propanethiol, 1-benzylamino-3-propanethiol, 1-allylamino-3-propanethiol and 1-propargylamino-3-propanethiol.

9. The process according to claim 1, wherein said compound of the formula (II) is used in an amount of from 0.5 to 10 moles per mole of the compound of the formula (I); wherein said base is used in an amount of 2 to 5 moles per mole of the compound of the formula (I); and wherein the reaction is carried out at a temperature of from $-10°$ to $50°$ C. for 0.5 to 10 hours.

10. The process according to claim 9, wherein said base is selected from the group consisting of sodium methoxide, sodium ethoxide, potassium methoxide, potassium ethoxide, sodium hydroxide, potassium hydroxide, calcium hydroxide, barium hydroxide, and magnesium hydroxide; and wherein said solvent is selected from the group consisting of methanol, ethanol, i-propanol, n-propanol, i-butanol, n-butanol, water, dimethyl sulfoxide, acetonitrile and dimethylformamide.

11. The process according to claim 10, wherein the compound of the formula (I) is selected from the group consisting of 2,2-dichloronitroethylene, 2,2-dibromonitroethylene, and 1,2,2-trichloronitroethylene; and wherein the compound of the formula (II) is selected from the group consisting of 1-amino-2-ethanethiol, 1-amino-3-propanethiol, 1-amino-4-butanethiol, 1-methylamino-3-propanethiol, 1-methylamino-4-butanethiol, 1-ethylamino-2-ethanethiol, 1-ethylamino-3-propanethiol, 1-isopropylamino-3-propanethiol, 1-hexylamino-3-propanethiol, 1-cyclohexylamino-3-propanethiol, 1-benzylamino-3-propanethiol, 1-allylamino-3-propanethiol and 1-propargylamino-3-propanethiol.

12. The process according to claim 11, wherein said compound of the formula (III) is selected from the group consisting of
tetrahydro-2-(nitromethylene)-1,3-thiazine,
tetrahydro-2-(nitro, chloromethylene)-2,3-thiazine,
2-(nitromethylene)-1,3-thiazolidine,
2-(hexahydronitromethylene)-1,3-thiazepine,
tetrahydro-3-methyl-2-(nitromethylene)-1,3-thiazine,
tetrahydro-3-ethyl-2-(nitromethylene)-1,3-thiazine,
tetrahydro-3-isopropyl-2-(nitromethylene)-1,3-thiazine,
tetrahydro-3-n-hexyl-2-(nitromethylene)-1,3-thiazine,
tetrahydro-3-cyclohexyl-2-(nitromethylene)-1,3-thiazine,
tetrahydro-3-benzyl-2-(nitromethylene)-1,3-thiazine,
tetrahydro-3-allyl-2-(nitromethylene)-1,3-thiazine,
tetrahydro-3-propargyl-2-(nitromethylene)-1,3-thiazine,
tetrahydro-3-methyl-2-(nitro, chloromethylene)-1,3-thiazine,
tetrahydro-3-ethyl-2-(nitro, chloromethylene)-1,3-thiazine,
tetrahydro-3-cyclohexyl-2-(nitro, chloromethylene)-1,3-thiazine,
tetrahydro-3-benzyl-2-(nitro, chloromethylene)-1,3-thiazine, tetrahydro-3-allyl-2-(nitro, chloromethylene)-1,3-thiazine,
tetrahydro-3-propargyl-2-(nitro, chloromethylene)-1,3-thiazine,
3-methyl-2-(nitromethylene)-1,3-thiazolidine, and
hexahydro-3-methyl-2-(nitromethylene)-1,3-thiazepine.

13. The process according to claim 1, wherein said base is selected from the group consisting of sodium methoxide, sodium ethoxide, potassium methoxide, potassium ethoxide, sodium hydroxide, potassium hydroxide, calcium hydroxide, barium hydroxide, and magnesium hydroxide; and wherein said solvent is selected from the group consisting of methanol, ethanol, i-propanol, n-propanol, i-butanol, n-butanol, water, dimethyl sulfoxide, acetonitrile and dimethylformamide.

* * * * *